United States Patent
Shipman

(10) Patent No.: US 8,834,426 B2
(45) Date of Patent: Sep. 16, 2014

(54) CATHETER AND TUBING RESTRAINING DEVICE AND PROTECTIVE COVER

(76) Inventor: Russell Shipman, York, ME (US)

(*) Notice: Subject to any disclaimer, the term of this patent is extended or adjusted under 35 U.S.C. 154(b) by 703 days.

(21) Appl. No.: 13/114,565

(22) Filed: May 24, 2011

(65) Prior Publication Data

US 2011/0313361 A1    Dec. 22, 2011

Related U.S. Application Data

(63) Continuation-in-part of application No. 12/706,445, filed on Feb. 16, 2010, now abandoned.

(60) Provisional application No. 61/255,270, filed on Oct. 27, 2009.

(51) Int. Cl.
| | |
|---|---|
| *A61M 5/32* | (2006.01) |
| *A61M 25/02* | (2006.01) |
| *A61L 29/06* | (2006.01) |
| *B29K 75/00* | (2006.01) |
| *B29C 51/16* | (2006.01) |
| *B29C 51/00* | (2006.01) |

(52) U.S. Cl.
CPC ............ *A61M 25/02* (2013.01); *B29K 2023/06* (2013.01); *B29K 2075/00* (2013.01); *B29C 51/16* (2013.01); *A61L 29/06* (2013.01); *A61M 2025/0253* (2013.01); *B29C 51/00* (2013.01)
USPC ........................................................ 604/180

(58) Field of Classification Search
CPC ..................... A61M 25/02; A61M 2025/0206; A61M 2025/0246; A61M 2025/0253; A61M 2025/0266; A61M 25/028; A61M 25/0293
USPC ................. 604/174–180, 351–352, 344, 343; 128/DIG. 6, 26
See application file for complete search history.

(56) References Cited

U.S. PATENT DOCUMENTS

| | | | | |
|---|---|---|---|---|
| 503,973 | A | | 8/1893 | Lovejoy |
| 4,480,639 | A | * | 11/1984 | Peterson et al. ......... 128/207.18 |
| 4,669,458 | A | | 6/1987 | Abraham et al. |
| 4,976,698 | A | * | 12/1990 | Stokley .................... 604/174 |
| 5,112,313 | A | | 5/1992 | Sallee |
| 5,116,324 | A | | 5/1992 | Brierley et al. |
| 5,342,317 | A | | 8/1994 | Claywell |
| 5,443,460 | A | * | 8/1995 | Miklusek .................... 604/530 |
| 5,707,348 | A | * | 1/1998 | Krogh ........................ 602/41 |
| 5,855,591 | A | | 1/1999 | Bierman |
| 5,885,254 | A | * | 3/1999 | Matyas ....................... 604/180 |
| 5,916,199 | A | * | 6/1999 | Miles ......................... 604/174 |
| 6,001,081 | A | * | 12/1999 | Collen ......................... 604/174 |
| 6,228,064 | B1 | | 5/2001 | Abita et al. |
| 6,322,539 | B1 | * | 11/2001 | Cook ........................ 604/174 |
| 6,582,403 | B1 | | 6/2003 | Bierman et al. |
| 6,809,230 | B2 | | 10/2004 | Hancock et al. |
| 7,198,066 | B2 | * | 4/2007 | Kagenow ................... 138/110 |
| 7,723,561 | B2 | * | 5/2010 | Propp .......................... 602/58 |
| 2006/0217669 | A1 | * | 9/2006 | Botha ........................ 604/177 |
| 2010/0217201 | A1 | * | 8/2010 | Lee et al. .................... 604/177 |
| 2011/0152779 | A1 | * | 6/2011 | Panotopoulos ............... 604/180 |

* cited by examiner

*Primary Examiner* — Andrew Gilbert
(74) *Attorney, Agent, or Firm* — Bourque and Associates, PA

(57) ABSTRACT

A restraining device for covering and protecting an intravenous access site or other access site that comprises an intravenous compartment hub portion or tubing device hub portion, coupled to a U-shaped portion coupled to a straight tubing portion. The combination of the compartment hub portion, U-shaped portion and straight tubing portion allows for an area where the intravenous catheter, catheter needle, luer lock and tubing can be placed, surrounding which is a flat, generally planar area that includes an adhesive backing for adhering the device to the skin of a patient. The anchoring protection device is a one-piece unit that is made from a thin, transparent, flexible material.

9 Claims, 4 Drawing Sheets

CATHETER AND TUBING RESTRAINING DEVICE AND PROTECTIVE COVER

CROSS REFERENCE TO RELATED APPLICATIONS

This application is a Continuation-in-Part of commonly assigned U.S. Utility patent application Ser. No. 12/706,445 filed on Feb. 16, 2010 titled "Anchoring And Protective Intravenous Shield", now abandoned, that in turn is related to and claims priority under 35 USC §119(e) to U.S. provisional Application No. 61/255,270 filed Oct. 27, 2009 entitled "Anchoring and Protective Intravenous Shield", which is incorporated fully herein by reference.

TECHNICAL FIELD

The present invention relates to a protective covering device and more particularly, relates to a shield or covering device for protecting, restraining and securing a catheter and/or tubes placed along an epidermal membrane.

BACKGROUND INFORMATION

The need to cover, restrain and protect the catheter and tubing site during medical treatment is well known. The catheter and tube needs to be protected from several adverse events. These events include catheter or tubing dislodgement causing infiltration of intravenous fluids as well as contamination from airborne sources that may lead to infections, disruption of a needed moisture barrier or preventing retrieval of fluids when suctioning is needed for medical treatments. The catheter or tubing site is at risk for unintended or purposeful dislodgement, which will interrupt the fluid administration or prevent fluid retrieval. This interruption will lead to delay of medical treatment, possible pain and infection in the patient, increased nursing time and higher medical costs due to the need to reinsert the catheter and/or tubing and due to the possibility of prolonged treatment time in hospital medical facility.

The prior art focuses on securing and protecting the intravenous area in the adult population. The prior art does not deal with the neonatal, pediatric, geriatric or other mammal population. In these populations, there is a higher risk of the patient grabbing, pulling or biting at the catheter and/or tubing resulting in dislodgment. Therefore, the prior art devices require improvements in order to solve the problems caused by use with all patients and in particular, in pediatric and geriatric patients.

A number of devices in the prior art disclose securing, protecting and allowing for visualization of the intravenous site. For example, in U.S. Pat. No. 4,669,458 to Abraham et al. and U.S. Pat. No. 6,809,230 to Hancock, a clear plastic window is adhesively applied to the IV site. U.S. Pat. No. 5,112,313 to Sallee and U.S. Pat. No. 5,116,324 to Brierley disclose a plastic cover over the IV site. These patents disclose non-flexible devices that allow the covering to be raised to allow inspection of the insertion site. Other patents such as U.S. Pat. No. 6,322,539 to Cook are intravenous guards shaped like animals to protect the IV site. They are held in place by a wristband. Other prior art patents are U.S. Pat. No. 503,973 to Lovejoy, U.S. Pat. No. 5,342,317 to Claywell and U.S. Pat. No. 6,228,064 to Abita. These patents disclose methods and apparatus for holding the intravenous catheter in place using a strap or band that may or may not be adhered to skin.

There are a number of disadvantages to each of the inventions in the prior art. The ability for the intravenous catheter to slide out of the venous or arterial lumen, thereby causing dislodgement and infiltration of fluids within the subcutaneous space leads to a caustic painful reaction and possible infection. Prior art issues also include lack of safety in the pediatric population, membranes that can be interrupted by tearing, and covers that do not anchor the intravenous catheter in place in a one-piece method. Therefore, there exists a need for a one-piece system and method of anchoring and protecting an intravenous catheter while also allowing for visual assessment of the intravenous catheter. The one-piece system should also be capable of covering other tubing devices, with slight modification, such as suctioning devices.

SUMMARY

This invention relates to a shield for protection of a peripheral venepuncture site for patients requiring intravenous fluids. In an exemplary embodiment of the present invention, the protection device allows for an area to be molded around an intravenous compartment hub, a lure lock and tubing as it sits on top of the skin. The molded area around the intravenous compartment hub allows for a flat surrounding area that facilitates anchoring and stabilization and specifically for preventing movement of the intravenous catheter out of the venous or arterial lumen.

In the exemplary embodiment of the present invention, the shield protects the intravenous site from being manipulated or tampered with. In one embodiment, a urethane material will be used for the shield, which is rip proof and access proof. The material will be resistant to tearing of the cover, thereby causing dislodgement of the intravenous catheter or other tubing. The combination of the unique material and the anchoring quality prevents removal.

In another embodiment of the present invention, the backing of the shield is coated with an adhesive backing that is scored to make at least two removable pieces. In a further embodiment of the present invention, the adhesive backing is scored into two equal halves, with the score line running down a centerline of the backing of the shield. The adhesive backing surrounds the body of the intravenous compartment hub and is fixably attached to the skin. In further embodiments of the present invention, the shield is moisture resistant and provides for protection from the surrounding environment. This will prevent contaminants from entering the venepuncture site causing infection.

In another embodiment of the present invention, the backing of the shield is coated with an adhesive backing that is scored to make at least two removable pieces. In a further embodiment of the present invention, the adhesive backing is scored into two equal halves, with the score line running down a center line of the backing of the shield. The adhesive backing surrounds the body of the intravenous compartment hub and is fixably attached to the skin. In further embodiments of the present invention, the shield is moisture resistant and provides for protection from the surrounding environment. This will prevent contaminants from entering the venepuncture site causing infection It is another objective of the invention to have a visually safe intravenous shield. Other IV covering are transparent but they are not tamper proof. They need to be covered by a thick wrap (coban) that is hiding the catheter from the patient. Other IV shields are not rip proof and can give the patient free access to the IV site. These covering methods are used regularly and have lead to unsafe IV sites. For example, swelling from infiltration of intravenous fluids or signs of infection would not be able to be visualized with such a wrap. In yet another embodiment of the present invention, the shield provides for visual safety of the intravenous compartment hub. In a preferred embodiment, the shield is a transparent shield that is tear proof, tamper proof and not easily removed.

In another embodiment of the current invention, the shield is manufactured in an economical and inexpensive manner. Production of the shield provides for a one-piece device.

In a further embodiment of the present invention, a protective shield for covering an intravenous catheter comprises a front side provided as a three-dimensional thermoplastic thermoformed urethane film that comprises an intravenous compartment hub portion configured and shaped to accommodate at least a portion of a catheter needle and a luer lock; a U-shaped portion, coupled to said intravenous compartment hub portion, said U-shaped portion configured and shaped to accept a first portion of a tube that is coupled to the luer lock; and a straight tubing portion, coupled to and extending from one portion of said U-shaped portion, and configured and shaped to accept a second portion of the tube; and a generally planar back side, wherein the back side is coated with an adhesive.

In this embodiment, the adhesive coating may include an acrylic pressure sensitive adhesive, which is covered by a removable protective layer. The removable protective layer may be scored to make at least two removable pieces. Alternatively, the protective layer may be one removable piece.

In another embodiment, the three-dimensional thermoplastic thermoformed urethane film of the front side of the protective cover includes a high density polyethylene carrier material that is resistant to ripping and tearing. The three-dimensional thermoplastic thermoformed urethane film of the front side of the protective shield is highly breathable and prevents maceration. The front side of the protective shield may be optically clear or may feature one or more colors.

In a preferred embodiment, the protective shield is designed wherein a width of the protective shield can range from 4-12 cm and a length of the protective shield can range from 6-12 cm.

In another embodiment, the protective shield further comprises a right angle portion, wherein the right angle portion is coupled to said straight tubing portion, and wherein said right angle portion is configured to accept a third portion of the tube.

In yet another embodiment, the front side includes a convex shape and the back side includes a concave shape, wherein the combination of the concave back side and the convex front side allows the protective shield to exhibit an appendage shaped curve that is configured to accommodate predetermined appendages.

In another embodiment of the present invention, a protective shield for covering a tubing site comprises a front side provided as a three-dimensional thermoplastic thermoformed urethane film that comprises: a hub portion configured and shaped to accommodate at least a portion of a tubing device; a U-shaped portion, coupled to said hub portion, said U-shaped portion configured and shaped to accept a first portion of a tube that is coupled to the tubing device; and a straight tubing portion, coupled to and extending from one portion of said U-shaped portion, and configured and shaped to accept a second portion of the tube; and a generally planar back side, wherein the back side is coated with an adhesive.

It is important to note that the present invention is not intended to be limited to a system or method which must satisfy one or more of any stated objects or features of the invention. It is also important to note that the present invention is not limited to the preferred, exemplary, or primary embodiment(s) described herein. Modifications and substitutions by one of ordinary skill in the art are considered to be within the scope of the present invention.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
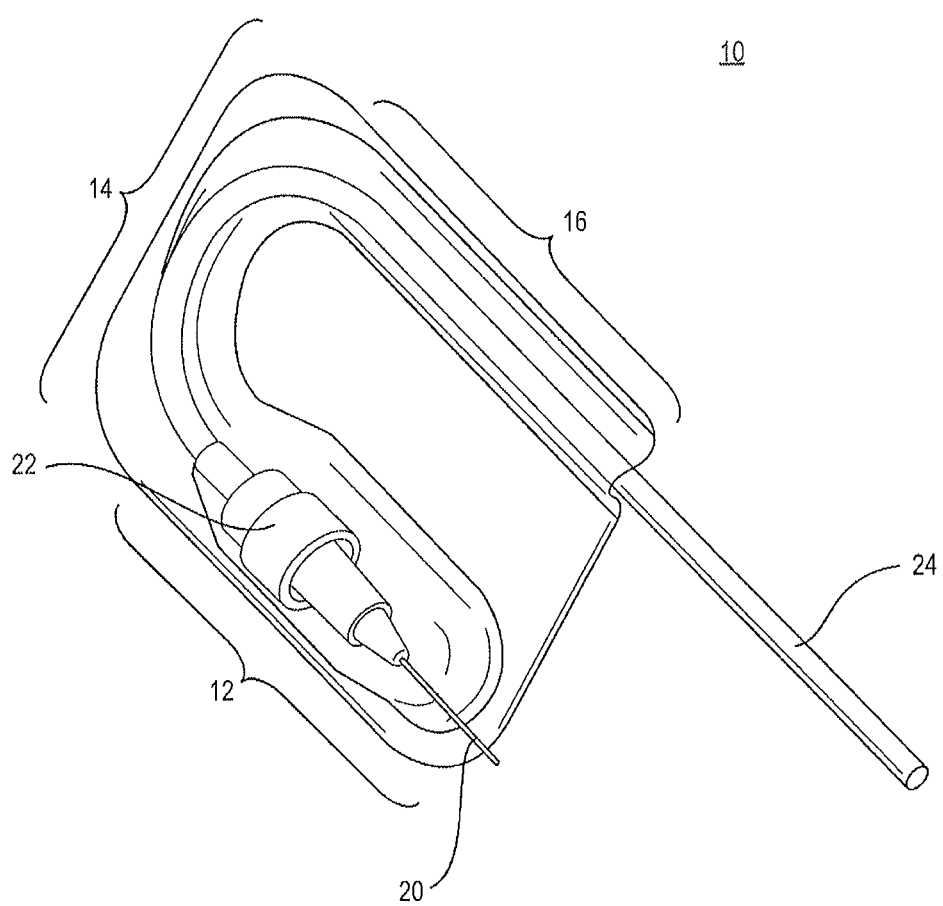
FIG. 1 is a detailed front view of an exemplary embodiment of the present invention.

The present invention features an anchoring intravenous shield 10, FIG. 1, which is attachable to the location of an intravenous catheter. An intravenous catheter may be located on the back of the hand, or alternatively at the antecubital site, scalp area, or another location. The anchoring intravenous shield 10 is comprised of three regions, the intravenous compartment hub portion 12, coupled to a U-shaped portion 14, which in turn is coupled to a straight tubing portion 16. The intravenous compartment hub portion 12 is designed to at least partially surround the catheter needle 20 and the luer lock 22. The U-shaped portion 14 and the straight tubing portion 16 are designed to at least partially surround the tube 24 of the catheter. The intravenous compartment hub portion 12 and the straight tubing portion 16 are essentially parallel to one another and are connected by the U-shaped portion 14, which completes essentially a 180 degree turn.

Figure 2A:
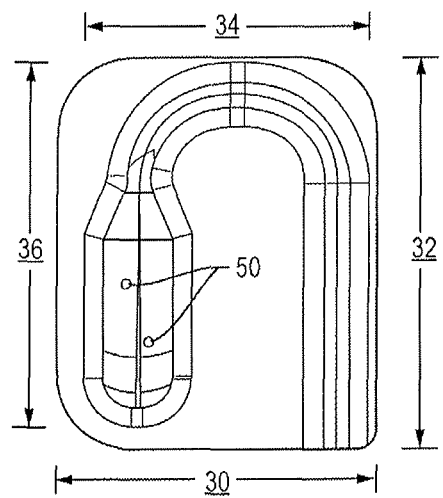
FIG. 2A is an above view perspective of an exemplary embodiment of the present invention.
Figure 2B:
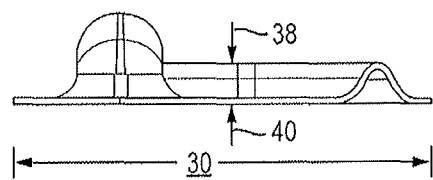
FIG. 2B is a view from a first side of the protection device.
Figure 2C:
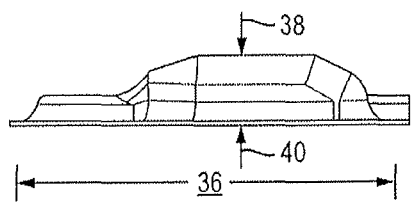
FIG. 2C is a view from a fourth side of the protection device.
Figure 3:
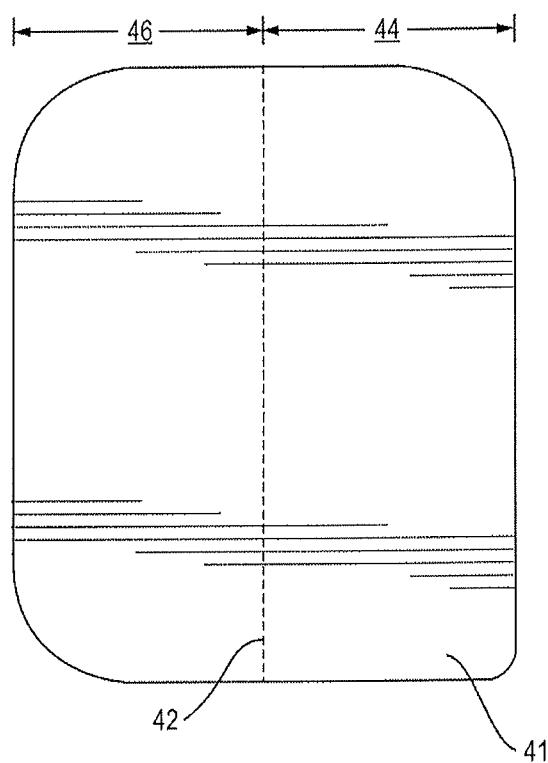
FIG. 3 is a detailed back view of an exemplary embodiment of the present invention.

The anchoring intravenous shield 10, FIG. 2A, features four edges, a first edge 30, a second edge 32, a third edge 34, and a fourth edge 36. The anchoring intravenous shield 10 also features two sides, a front side 38, FIG. 2B, and a back side 40. The back side 40 comes into contact with a surface (not shown) of the patient's skin and features an adhesive backing 41, FIG. 3. The adhesive backing 41 typically includes a releasable paper or plastic covering (removable protective layer) which is preferably scored as shown for example at 42, and which divides and exposes the adhesive backing covering into two pieces, a first adhesive backing piece 44 and a second adhesive backing piece. In one embodiment of the present invention, the adhesive backing is scored along a center line 42 but this is not a limitation of the invention. It is also contemplated and within the scope of the invention that the removable protective layer may be a one piece peel off, which may include a tab in one or more corners to facilitate gripping and removing the removable protective layer.

The following steps are taken in order to secure the anchoring intravenous shield 10. After insertion of the catheter needle into the patient, a first adhesive backing covering piece is removed and the catheter needle 20 and luer lock 22 are secured in place in the intravenous compartment hub portion 12. A portion of the tube 24 may also be secured at this point. This creates an anchoring quality, which prevents the intravenous catheter from sliding out of the venous lumen and dislodging. Then, the second adhesive covering piece is removed and the intravenous tubing is placed into the U-shaped portion 14 and the tubing portion 16. The adhesive backing 41 is thus now fully secured to the skin of the patient. The anchoring intravenous shield 10 is essentially immovable and maintains the intravenous catheter needle in place. Other methods of adhering the anchoring intravenous shield are within the scope of the present invention.

The anchoring intravenous shield 10 is preferably made from urethane, although other materials are within the scope of the current invention. The urethane is thin, flexible and transparent. The transparency of the material allows for complete visualization of the insertion point, the catheter needle and the luer lock, thereby allowing a medical professional to view the status of the intravenous catheter. The urethane material also allows the anchoring intravenous shield to conform to the shape of the application area, whether it is the hand, or another area of the patient. The urethane material also allows the entire front side to be formed from one-piece of material, which allows for simple manufacture and simple application to a patient. In a preferred embodiment of the present intention, the material is tamper proof and can not be torn. Additionally, the material is preferably moisture proof, contaminant proof, and bacterial proof, thereby keeping the intravenous site safe from harmful substances.

In another embodiment of the present invention, the front side contains one or more breathing holes or apertures 50 to allow moisture and normal skin perspiration to vent outside of the enclosure created by the intravenous compartment hub portion. The breathing holes may be located along the front side of the intravenous compartment hub portion. The front side creates an essentially airtight shield within the closed cover and the breathing holes can be used to allow air circulation. The breathing holes may be circular in shape.

Figure 4:
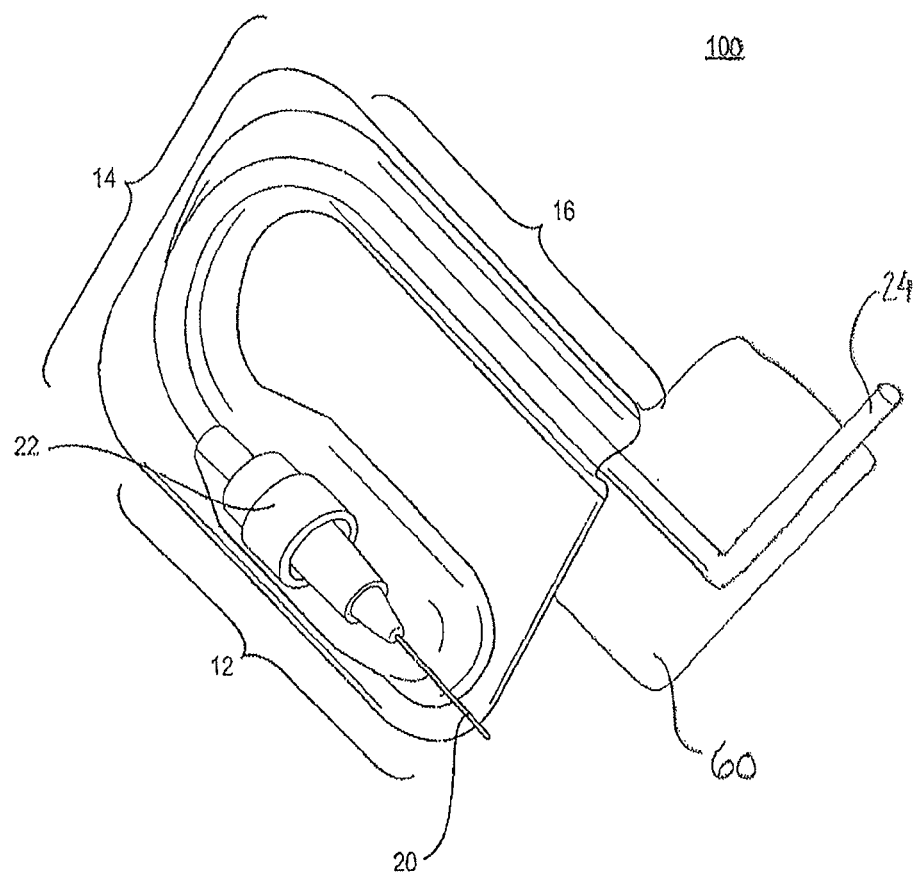
FIG. 4 is a detailed front view of another embodiment of the present invention.

In another embodiment of the present invention a restraining protective cover 100, FIG. 4, for catheters and/or other tubing devices features a front side 38 and a back side 40. The front side 38 is a molded three dimensional thermoformed thermoplastic cover 100. The cover 100 is preferably made from a urethane film material. The urethane film material is supported by a 2 mil high density polyethylene (HDPE) carrier, which allows for ease of film use and converting, which benefits the replicating and manufacturing process by easing the processing of the product from sheet stock. The back side 40 is preferably coated with a medical acrylic pressure sensitive adhesive. The cover 100 also has good die cutting ability. The material used for the cover 100 is highly breathable and features a moisture wicking quality. The breathable urethane film wicks moisture away from the epidermis, thereby preventing maceration. The material has properties that allows for movement of high moisture to low moisture, while also keeping the cover in place. Preferably, the movement of moisture is only permitted from inside the cover to outside the cover. Moisture and water is not permitted to travel from outside the cover into the cover. The cover 100 is also very soft and comfortable with a skin-like feel. The cover 100 and the adhesive are preferably non-irritating and non-sensitizing. As a result, the cover 100 can be used in extended contact with the epidermis where breathability matters, such as in an open wound area.

In this embodiment, the cover is preferably optically clear to allow for ease of visual examination of the underlying catheter and/or tubing device. Alternatively, the cover may be colored in one solid color or with various artwork or designs to enhance pediatric acceptance of the cover. The cover 100 will be sized in various sizes to accommodate neonatal, toddlers, children, teenagers, adults, geriatric, and also the veterinarian population. In one embodiment, there would be ten different sizes available for patients. Sizes would range from 4-12 cm in width and 6-12 cm in length.

The cover features a non-planar design that includes a U-shaped portion 14, an IV compartment hub portion 12 and a straight tubing portion 16. The U shaped portion 14 is coupled to the IV compartment hub portion 12 and the straight tubing portion 16. The U-shaped portion 14 is configured to accept a first portion of a tube that is coupled to a luer lock or some other similar medical device (22). The luer lock (22) is contained within the IV compartment hub portion 12. The straight tubing portion 16 is configured to accept a second portion of the tubing. The cover 100 may also feature an optional right angle portion 60, which is coupled to the straight tubing portion 16 and which is designed to further secure a portion of the tubing. The right angle portion 60 is configured to hold a portion of the tubing 24 at a right angle to the straight tubing portion 16. Although the right angle portion 60 is shown in a direction to the right, it is also contemplated and within the scope of the current invention that the right angle portion 60 could hold the tubing portion in the opposite direction. The inclusion of all of these portions is not intended to be a limitation of the present invention. For example, the cover 100 may not include the IV compartment hub portion 12 when the cover 100 is used with another tubing device, such as a device used for suctioning. When used with another tubing device, the IV compartment hub portion 12 may be a hub portion that is sized to cover a tubing device.

The cover 100 will preferably feature an anthropomorphic (appendage shaped) design, wherein the back side 40 features a slight concave shape and the front side 38 features a slight convex shape. The shape allows the cover 100 to accommodate appendages such as a wrist, an arm, a thigh, an ankle, the neck, airways, or any other orifice. The cover may also feature virucidal and/or bactericidal properties.

Accordingly, the present invention provides a three dimensional thermoformed thermoplastic cover with a pressure sensitive adhesive that can be used to restrain and protect a catheter and tubing site. It is contemplated and within the scope of the current invention, that the cover could be modified slightly and used with other tubing devices, such as NG tubes, NJ tubes, G-tubes, J-tubes, and GJ tubes.

Accordingly, the present invention provides a novel anchoring protection device for covering and protecting an intravenous access site. The anchoring and covering device comprises an intravenous compartment hub portion, coupled to a U-shaped portion coupled to a straight tubing portion. The combination of the compartment hub portion, U-shaped portion and straight tubing portion allows for an area where the intravenous catheter, catheter needle, luer lock and tubing can be placed, surrounding which is a flat, generally planar area that includes an adhesive backing for adhering the device to the skin of a patient. The anchoring protection device is a one-piece unit that is made from a thin, transparent, flexible material that also "breaths" and allows for extended use without damage to the underlying skin.

Modifications and substitutions by one of ordinary skill in the art are considered to be within the scope of the present invention which is not to be limited except by the allowed claims and their legal equivalents.

The invention claimed is:

1. A protective shield for covering an intravenous catheter during use of the intravenous catheter in contact with a patient's skin, the protective shield comprising:
    an intravenous hub cavity portion, configured and shaped to accommodate at least a portion of a catheter needle and a catheter luer lock;

a U-shaped cavity portion having first and second ends, a first end of said U-shaped cavity portion coupled to said intravenous hub cavity portion, said U-shaped cavity portion configured and shaped to accept a first portion of the intravenous catheter tube that is coupled to the catheter luer lock;

a straight tubing cavity portion, coupled to and extending from the second end of said U-shaped cavity portion, and configured and shaped to accept a second portion of the intravenous catheter;

the protective shield having a back side surface having a planar portion configured to contact a patient during application of the protective shield to a patient's underlying skin around the intravenous catheter;

the protective shield having a front side surface opposite from the back side surface;

wherein the protective shield is a flexible, thermoformed, thermoplastic, having a three-dimensional, thermoformed cavity portion in said back side surface, the three-dimensional, thermoformed cavity portion forming the intravenous hub cavity portion, the U-shaped cavity portion and the straight tubing cavity portion; and wherein the back side surface includes an adhesive layer coated on the planar portion of the back side surface and wherein said three-dimensional, thermoformed cavity portion in said back side surface does not include said adhesive layer.

2. The protective shield of claim 1 wherein the adhesive layer includes acrylic pressure sensitive adhesive coating which is covered by a removable protective layer.

3. The protective shield of claim 2 wherein the removable protective layer is scored to make at least two removable pieces.

4. The protective shield of claim 2 wherein the removable protective layer is one removable piece.

5. The protective shield of claim 1, wherein the front side surface of the protective shield is optically clear.

6. The protective shield of claim 1, wherein the front side surface of the protective shield features one or more colors.

7. The protective shield of claim 1, wherein a width of the protective shield is between 4-12 cm and a length of the protective shield is between 6-12 cm.

8. The protective shield of claim 1, further comprising:

a right angle cavity portion, wherein the right angle cavity portion is coupled to said straight tubing cavity portion, and wherein said right angle cavity portion is configured to accept a third portion of the intravenous catheter coupled to the second portion of the intravenous catheter.

9. The protective shield of claim 1, wherein the front side surface comprises a convex shape and the back side surface comprises a concave shape, wherein the combination of the concave shaped back side surface and the convex shaped front side surface is configured to provide protective shield having an appendage shaped curve that is configured to accommodate predetermined appendages.

\* \* \* \* \*